United States Patent [19]

Klemm

[11] Patent Number: Plant 7,208

[45] Date of Patent: Apr. 3, 1990

[54] GERANIUM PLANT NAMED MARLICAT

[75] Inventor: Siegfried Klemm, Stuttgart, Fed. Rep. of Germany

[73] Assignee: Selecta Klemm KG, Stuttgart-Muhlhausen, Fed. Rep. of Germany

[21] Appl. No.: 241,095

[22] Filed: Sep. 6, 1988

[51] Int. Cl.[4] ..... A01H 5/00

[52] U.S. Cl. ..... Plt./68

[58] Field of Search ..... Plt. 68

*Primary Examiner*—James R. Feyrer

*Attorney, Agent, or Firm*—Charles W. Rummler

[57] ABSTRACT

A new and distinctive geranium variety particularly distinguished by its clear salmon-pink flowers blooming over foliage of medium sized, nearly black, zonated leaves, the flower clusters comprising about seventy-five very large florets, each floret having a diameter of about 5.5 cm. This plant is further distinguished by its continuous and profuse blooming habit from early Spring through midseason and into late Fall; and its vigorous and spreading growth habit to a height of about 35 cm. with abundant foliage of medium leaf size standing about 20 cm. above the soil.

1 Drawing Sheet

BACKGROUND OF THE NEW PLANT

My new geranium cultivar originated as a sport of the variety 'Palais' growing in my nursery at Stuttgart, West Germany, and crossed by an unknown pollen parent. The seed parent 'Palais' was cultivated primarily for seed collection and the present hybrid was discovered in 1985 and selected for propagation and test because of the delightful salmon-pink coloration of its very large flower clusters. Propagation was done under my direction by means of cuttings with such success that propagation was continued on at Stuttgart in the same manner through several successive generations, which demonstrated that the distinctive characteristics and homogeneity of this variety would hold true from generation to generation and appears to be firmly fixed.

DESCRIPTION OF THE DRAWINGS

My new geranium discovery is illustrated by the accompanying full color photographic drawing, which shows a potted plant in full bloom with flower clusters in various stages of development, as well as umbel-formed clusters of buds in several stages of development, as well as the nature of the foliage and the growth characteristics of this new variety, the color rendition being as nearly true to that herein specified as is reasonably possible to obtain by conventional photographic procedures.

DESCRIPTION OF THE NEW PLANT

The following is a detailed description of my new geranium cultivar as observed at my nursery in Stuttgart in the Spring of 1988, with color designation according to The R.H.S. Colour Chart of The Royal Horticultural Society at London, England.

THE PLANT

Origin: Seedling.

Parentage:

*Seed parent.*—'Palais' (unpatented).

*Pollen parent.*—Unknown.

Classification:

*Botanic.*—*Pelargonium zonale* Hybrid.

*Commercial.*—Geranium.

Form: Bush.

Height: About 30 to 35 cm.

Main stem length: Depends upon the age of the plant. For this variety, the stems can grow to a length of about 17 cm.

Branching character: Normal.

Growth: Vigorous and spreading with good strength.

Foliage:

*Quantity.*—Abundant.

*Size of leaf.*—About 7.5 cm. long and about 6.5 cm. wide.

*Leaf shape.*—Orbiculate with bicrenate margins.

*Texture.*—Smooth.

*Ribs and veins.*—Seven main veins on each leaf.

*Color.*—Upper side: Very dark green with a light center. Under side: Very light green.

THE BUD

Size: Large.

*Diameter.*—About 12 mm.

*Length.*—About 14 to 18 mm.

Shape: Elliptic with pointed apex.

Rate of opening: Medium.

Color of petals: When sepals first divide, white to pink. When petals begin to unfurl, salmon with a white border.

Sepals:

*Number.*—Five.

*Shape.*—Lanceolate. The sepals stand up when the flowers open.

*Color.*—Inside and outside: Green.

Flower stalk:

*Length.*—About 17 cm.

*Character.*—Erect and rigid.

*Color.*—Dark brown.

THE INFLORESCENCE

Blooming habit: Continuous and profusely from early Spring to late Fall.

Number of florets per cluster: About seventy-five.

Size of floret: Very large.

*Diameter.*—About 5.5 cm.

*Depth.*—About 1 cm.

Borne: Singly on the stem of an umbel cluster.

Shape: When bloom first opens, cup-shaped. when bloom matures, flat cup.

Petalage:

*Number of petals.*—Six or seven.

*Arrangement.*—Regularly imbricated.

*Form.*—Wide, almost round, with entire margins.

*Texture.*—Soft.

*Appearance.*—Satiny.

*Color.*—RHS 41-C at start, but goes to salmon-pink and the border of the petals is white.

Flower stalk:

*Length.*—About 17 cm.

*Color.*—Dark brown.

*Character.*—Sturdy and upright.

Persistence: The floret petals fall down after about five or six days, but the bloom is long lasting so that plants with old flowers look clean and tidy as the new flowers appear.

REPRODUCTIVE ORGANS

Stamens:

*Number.*—Seven.

*Arrangement.*—Around the ovaries.

*Anthers.*—Size: About 1.5 mm. Color: Light brown.

*Filaments.*—Length: About 3 to 4 mm. Color: Light brown.

*Pollen.*—Color: Orange.

Pistil:

*Number.*—One.

*Style.*—Length: About 4 mm. Color: Light green.

*Stigma.*—Color: Light frosted Salmon-glas.

Character of ovary: Normal.

THE FRUIT

Fertility: The fruit is very fertile.

Shape: Ovoid.

Color at maturity: Dark brown.

This new variety is very striking because of the beautiful, clear flower coloration, the flowers appearing early in the Spring and lasting long. The foliage has very good zonation and no Botrytis disease has been seen in this variety.

I claim:

1. A new and distinctive geranium cultivar substantially as herein shown and described, characterized by the large size of its clear, pink colored flower clusters, the very large size of the florets with regularly imbricated and wide, almost round, petals, its abundant foliage of medium sized leaves, and its vigorous, upright and strong growth habit.

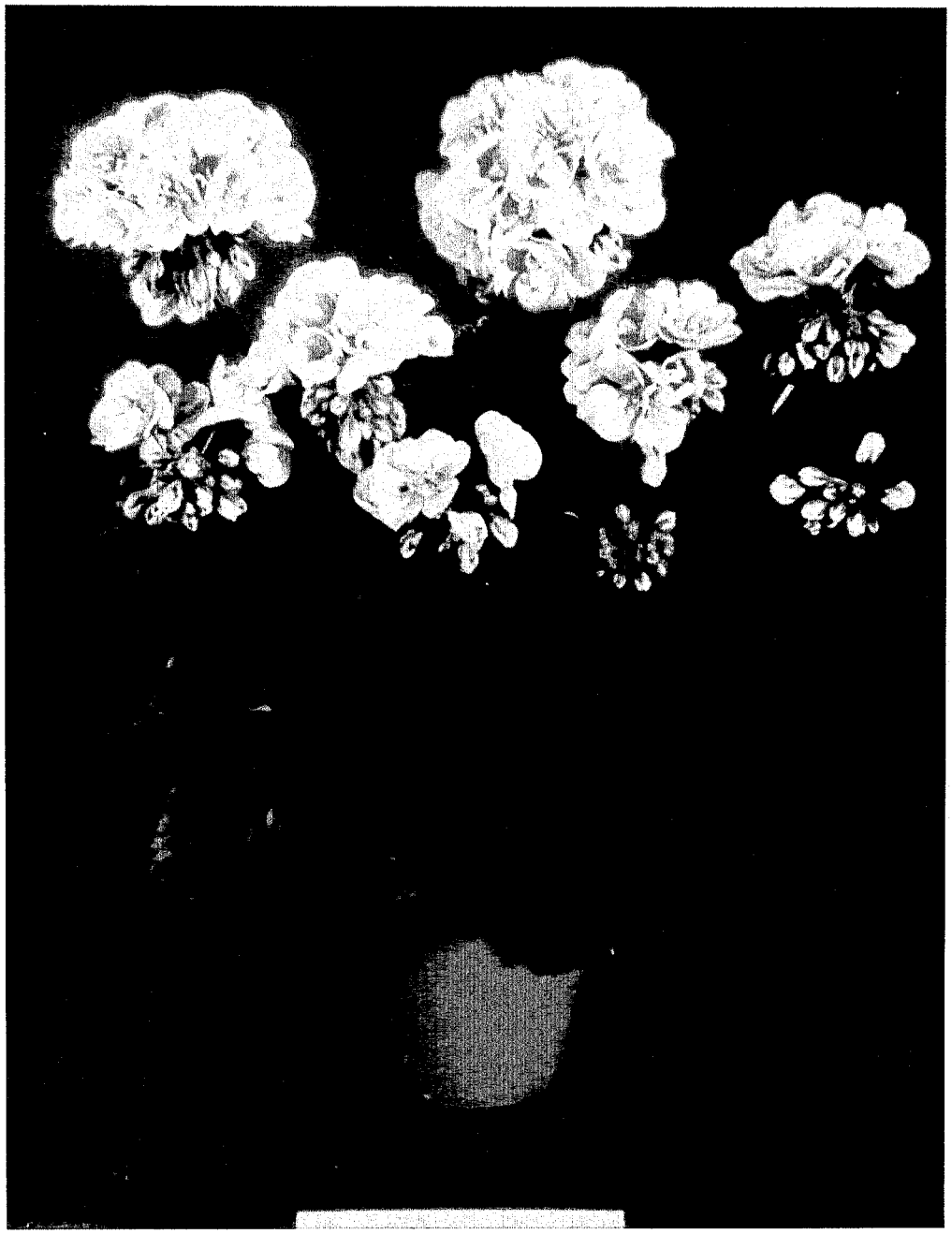

* * * * *